(12) United States Patent
Moeskops et al.

(10) Patent No.: US 9,750,572 B2
(45) Date of Patent: Sep. 5, 2017

(54) CUTTING HEAD FOR A DEVICE FOR CUTTING HAIR

(71) Applicant: KONINKLIJKE PHILIPS N.V., Eindhoven (NL)

(72) Inventors: Bastiaan Wilhelmus Maria Moeskops, Eindhoven (NL); Mark Thomas Johnson, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 87 days.

(21) Appl. No.: 14/758,598

(22) PCT Filed: Dec. 27, 2013

(86) PCT No.: PCT/IB2013/061355
§ 371 (c)(1),
(2) Date: Jun. 30, 2015

(87) PCT Pub. No.: WO2014/108783
PCT Pub. Date: Jul. 17, 2014

(65) Prior Publication Data
US 2015/0359592 A1    Dec. 17, 2015

Related U.S. Application Data

(60) Provisional application No. 61/750,864, filed on Jan. 10, 2013.

(51) Int. Cl.
*A61B 18/18* (2006.01)
*A61B 18/20* (2006.01)
(Continued)

(52) U.S. Cl.
CPC ........ *A61B 18/203* (2013.01); *B23K 26/0626* (2013.01); *B23K 26/073* (2013.01);
(Continued)

(58) Field of Classification Search
CPC . A61B 18/203; B23K 26/0626; B23K 26/073
See application file for complete search history.

(56) References Cited

U.S. PATENT DOCUMENTS

| 5,993,440 A | 11/1999 | Ghassemi | |
|---|---|---|---|
| 7,699,058 B1 | 4/2010 | Jay | |
| 2008/0255548 A1* | 10/2008 | Van Hal | A61B 18/203 606/10 |

FOREIGN PATENT DOCUMENTS

| WO | 9106406 A1 | 5/1991 |
|---|---|---|
| WO | 9216338 A1 | 10/1992 |

(Continued)

*Primary Examiner* — Robert N Wieland

(57) ABSTRACT

The present application relates to a cutting head for a device for cutting hair. The cutting head has a laser generator (2) and an optical system (3). The optical system is configured to focus a laser beam (4) generated by the laser generator and direct the laser beam along an optical axis (16) across a cutting zone (8) in the cutting head. The laser generator and optical system are configured such that, in a focus spot (15) of the laser beam, a dimension of the focus spot, a power density of the laser beam and the numerical aperture of the laser beam are such that, when a hair is received in the cutting zone, the power output of the laser generator is minimized while ensuring that, for a predetermined exposure time, the hair received in the cutting zone is cut by optical absorption. The present application also relates to a device for cutting hair and a method of controlling a cutting head for a device for cutting hair.

15 Claims, 1 Drawing Sheet

(51) Int. Cl.
*B23K 26/06* (2014.01)
*B23K 26/073* (2006.01)
*A61B 18/00* (2006.01)

(52) U.S. Cl.
CPC ............... *A61B 2018/00452* (2013.01); *A61B 2018/00476* (2013.01)

(56) References Cited

FOREIGN PATENT DOCUMENTS

| | | |
|---|---|---|
| WO | 9533600 A1 | 12/1995 |
| WO | 0062700 A1 | 10/2000 |
| WO | 2005011510 A1 | 2/2005 |
| WO | 2007039854 A1 | 4/2007 |
| WO | 2008120141 A2 | 10/2008 |
| WO | 2014020512 A1 | 2/2014 |

* cited by examiner

CUTTING HEAD FOR A DEVICE FOR CUTTING HAIR

This application is the U.S. National Phase application under 35 U.S.C. §371 of International Application No. PCT/IB2013/061355, filed on Dec. 27, 2013, which claims the benefit of U.S. Provisional Application No. 61/750,864 filed on Jan. 10, 2013. These applications are hereby incorporated by reference herein.

FIELD OF THE INVENTION

The present application relates to a cutting head for a device for cutting hair. The present application also relates to a device for cutting hair and a method of controlling a cutting head for a device for cutting hair.

BACKGROUND OF THE INVENTION

It is known to provide a shaver or razor that relies on a laser for cutting hair rather than an arrangement of cutting blades. Shavers without blades have fewer moving parts and so wear is reduced, which provides an advantage over mechanical shavers. Furthermore, the use of a laser can reduce skin irritation as there are no sharp objects that contact the skin surface. Laser shavers work by either optical absorption or by creating laser induced optical breakdown of the hair. With optical absorption, hair is exposed to a laser beam and absorbs the energy of the beam, causing the hair to be vaporised and/or severed. With laser induced optical breakdown of the hair, the hair is cut by cavitation and/or the generation of shockwaves.

Shaving performance is typically measured by two criteria closeness of shave and irritation of the skin. Therefore, a good performing shaver should minimise the remaining hair length by positioning the laser as close as possible to the skin. However, this may cause more skin irritation if heat and energy from the laser is incident on the skin. It is necessary to protect the skin from contact with the laser beam to avoid damaging or irritating the skin being shaved. Hair trimmers or groomers are used to trim hair to a constant length, so although closeness is not a major performance factor, uniformity of remaining hair length is desirable.

It is known, for example from WO 92/16338, to generate a laser beam that is positioned parallel to the skin and perpendicular to the stroke direction to cut hairs as the shaver is moved over the skin. However, Gaussian theory dictates that laser beams have a natural intensity variation along their length. Furthermore, when hair is cut with a laser a number of parasitic physical and chemical phenomena may occur that impede the hair cutting process.

SUMMARY OF THE INVENTION

It is an object of the invention to provide a head unit for device for cutting hair which substantially alleviates or overcomes the problems mentioned above, amongst others.

According to the present invention, there is provided a cutting head for a device for cutting hair, comprising a laser generator and an optical system configured to focus a laser beam generated by the laser generator and direct the laser beam along an optical axis across a cutting zone in the cutting head, wherein the laser generator and optical system are configured such that, in a focus spot of the laser beam, a dimension of the focus spot, a power density of the laser beam and a numerical aperture of the laser beam are such that, when a hair is received in the cutting zone, the power output of the laser generator is minimised whilst ensuring that, for a predetermined exposure time, the hair received in the cutting zone is cut by optical absorption.

By configuring one or more dimensions of the focus spot, the power density of the laser beam and the numerical aperture of the laser beam it is possible to minimise or eliminate a number of parasitic physical and chemical phenomena that impede the hair cutting process. By selecting predetermined parameters it is possible to ensure that hair received in the cutting zone is cut with the maximum efficiency.

The optical system may be configured such that the numerical aperture is equal to or less than 0.8, preferably equal to or less than 0.6, and more preferably equal to or less than 0.4.

The above parameters prevent parts of the hair to be cut from being out of the laser focus while the centre of the hair is in focus.

The optical system may be configured such that the vertical focus spot size of the focus spot is equal to or less than 0.2 mm, preferably equal to or less than 0.1 mm, and more preferably equal to or less than 0.05 mm.

With a vertical focus spot size below the given threshold parameters it has been found that the effective rate of cutting a hair is maximised. This prevents an unnecessarily larger fraction of the hair from being evaporated through the provision of a laser beam having a too large vertical focus spot size.

The optical system may be configured such that the horizontal focus spot size of the focus spot is between 0.05 mm and 1 mm, preferably between 0.1 mm and 0.5 mm, and more preferably between 0.15 mm and 0.3 mm.

The above arrangement enables the entire width of the beam to impact the hair, maximising the photons absorbed in the hair. Therefore the efficiency of the cutting process may be maximised. Furthermore, by providing a horizontal spot size with the above threshold values, the beam is able to extend across the width of the hair such that the entire width of the hair is exposed to the laser beam.

The power density of the laser beam in the focus spot may be equal to or greater than 1000 W/cm$^2$, preferably equal to or greater than 5000 W/cm$^2$, and more preferably equal to or greater than 50000 W/cm$^2$.

By providing a power density above the threshold value the desired effect of evaporation of hair can be achieved, whilst melting of the hair is prevented. Melting of the hair is not desired since it does not always lead to hair cutting, but does consume laser energy, thus reducing the efficiency of the cutting action.

The laser generator may be configured to produce a continuous output beam. Alternatively, the laser generator may be configured to produce a pulsed output beam. The laser generator may be configured to produce the laser beam with a pulse duration of equal to or greater than 0.1 μs, preferably greater than 1 μs, and more preferably greater than 100 μs.

By providing a pulse duration of greater than or equal to the above threshold values it is possible to minimise parasitic plasma formation, and to ensure that the laser beam delivers sufficient energy to cut the hair.

The optical system may be configured such that, during use, the position of the optical axis of the laser beam defined in the cutting head is maintained.

Maintaining the position of the optical axis ensures that the cutting height remains constant. Furthermore, the laser beam is not directed towards a user's skin which may cause irritation.

The cutting head may further comprise a cutting surface against which, during use, the skin of a user is locatable. The optical axis may extend substantially parallel to the cutting surface.

With the provision of a cutting surface the skin of a user is prevented from entering the cutting zone. Therefore, it is not necessary to maintain the properties within set parameters for when the laser is directed in a direction towards a user's skin. This means that it is possible to set the parameters of the laser beam to cut hair with the greatest efficiency.

The cutting surface may be defined by a spacer disposed adjacent to the cutting zone to contact a user's skin during use to maintain spacing between a user's skin and the laser beam in the cutting zone.

Maintaining separation between the laser beam and the skin is important for minimising the irritation caused to the skin.

The optical system may further comprise a first reflective element to direct the laser beam across the cutting zone.

The optical system may further comprise a second reflective element disposed on an opposite side of the cutting zone to the first reflective element to direct the laser beam away from the cutting zone.

In another embodiment, the optical system may further comprise a second reflective element disposed on an opposite side of the cutting zone to the first reflective element which is configured to reflect the laser beam back across the cutting zone.

This provides a second cutting section of the laser beam that passes through the cutting zone, therefore improving the cutting performance of the shaver.

According to another aspect of the invention, there is provided a device for cutting hair comprising a cutting head comprising a laser generator and an optical system configured to focus a laser beam generated by the laser generator and direct the laser beam along an optical axis across a cutting zone in the cutting head, wherein the laser generator and optical system are configured such that, in a focus spot of the laser beam, a dimension of the focus spot, a power density of the laser beam and a numerical aperture of the laser beam are such that, when a hair is received in the cutting zone, the power output of the laser generator is minimised whilst ensuring that, for a predetermined exposure time, the hair received in the cutting zone is cut by optical absorption.

The device for cutting hair may comprise two or more interchangeable cutting heads. Therefore, a cutting head may be replaced after it has become worn, or interchanged with another cutting head having a different arrangement.

According to another aspect of the invention, there is provided a method of controlling a cutting head for a device for cutting hair, comprising a laser generator and an optical system configured to focus a laser beam generated by the laser generator and direct the laser beam along an optical axis across a cutting zone in the cutting head, the method comprising setting, in a focus spot of the laser beam, a dimension of the focus spot, a power density of the laser beam and the numerical aperture of the laser beam such that, when a hair is received in the cutting zone, the power output of the laser generator is minimised whilst ensuring that, for a predetermined exposure time, the hair received in the cutting zone is cut by optical absorption.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
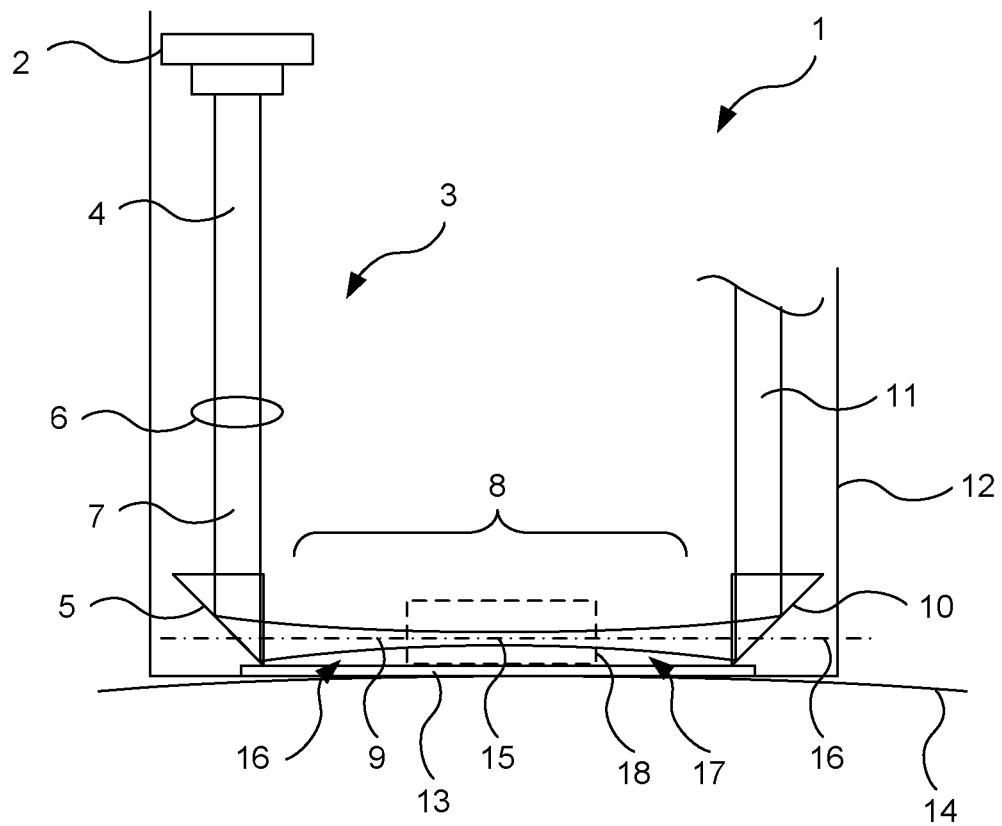
FIG. 1 shows a schematic diagram of a head unit for a device for cutting hair.

FIG. 1 shows a schematic diagram of a head unit 1 for a device for cutting hair. The head unit 1 forms a laser shaver cutting head of a laser shaver. The head unit 1 comprises a laser generator 2, acting as a laser source, and an optical system 3. The laser generator 2 in the present arrangement is a diode. The laser source 2 emits a laser beam 4. The laser beam 4 follows an optical path from the laser source 2 in the head unit 1. The laser beam 4 is directed towards the optical system 3. The optical system 3 has a first reflective element 5 and a collimating lens 6. The laser beam 4 is directed towards the first reflective element 5 via the collimating lens 6. The collimating lens 6 reduces or eliminates the divergence of the beam. The collimated section or path 7 of the beam 4 is then reflected by the first reflective element 5. In the present arrangement, the collimated section 7 of the beam 4 is reflected through 90 degrees, although it will be understood that the beam may be reflected through an alternative angle.

The head unit 1 has a cutting zone 8 in which hairs are received to be cut. The reflected beam, acting as a cutting section or path 9 of the beam 4 travels across the cutting zone 8 in which hairs are received to be cut by optical absorption caused by the cutting section 9 of the laser beam 4. A second reflective element 10 is positioned on the opposite side of the cutting zone 8 to reflect the laser beam 4 along an exit section or path 11 that travels away from the cutting zone 8. The exit section 11 of the beam 10 may then be absorbed within an energy dissipater or similar device (not shown) to prevent damage being caused by the energy of the remaining laser beam 10.

The cutting head 1 further comprises a body 12 with a spacer 13 that contacts a section of the skin 14 of a user to maintain protective separation between the laser beam 4 and the skin 14. The spacer 13 comprises a cutting surface against which a user's skin is locatable. The spacer 13 comprises at least one opening (not shown). The spacer 12 allows hairs (not shown) to protrude into the cutting zone 8. The cutting zone 8 is defined in the region above the spacer 13 where the cutting section 9 of the laser beam 4 crosses. The spacer 13 comprises a single, elongate opening (not shown) that is parallel to the cutting section 9 of the laser beam 4 through which hairs are received for cutting. Alternatively, the spacer 13 may have an alternative arrangement, such as a plurality of circular, hexagonal or similar openings (not shown) through which the hair is received into the cutting zone 8. Alternatively, the spacer 13 may comprise a comb with a plurality of teeth that manipulate the hairs into the cutting zone 8.

The first and second reflective elements 5, 10 are positioned on opposite sides of the body 12. The cutting zone 8 is defined in the region between the first and second reflective elements 5, 10. The diode 2 and collimating lens 6 are positioned on one side of the body 12, aligned with the first reflective element 5.

Gaussian theory dictates that laser beams have a natural intensity variation along their length. Beams will have a focal point where the laser beam has maximum intensity (power per unit area) and minimum width, meaning the focal point is the most effective part of the laser beam for severing hair by optical absorption. On the other hand, parts of the laser beam furthest from the focal point will have a larger width and therefore a more distributed intensity and will not be as effective at severing hair because the energy of the laser beam is incident over a larger area of hair. Therefore, there is a variation in hair severing performance along the optical axis of a laser beam. Due to the natural divergence of Gaussian laser beams it is impossible to achieve a uniform beam thickness along an optical axis.

Between the first and second reflective elements 5, 10 the cutting section 9 of the laser beam 4 will conform to Gaussian theory and will comprise a 'focal point' 15, or waist, located along an optical axis 16 of the beam 4. The focal point 15 is the position of maximum intensity and minimum width and the most effective part of the beam 4 for severing hair because the laser beam energy is concentrated on a smaller area of the hair to be severed, increasing the rate of optical absorption. The regions 16, 17 either side of the waist 15 have a larger beam width and lower intensity so are less effective for severing hair because the laser beam energy is distributed over a larger area of the hair. This arrangement may lead to a variation in cutting performance across the cutting zone 8 as the focal point 15 of the laser beam 4 severs hairs more cleanly and at a different length to the other parts 16, 17 of the cutting section 9 of the laser beam 4.

Gaussian beam theory can be used to determine the natural variation in intensity along a beam by considering the change in beam width (cross-sectional area) caused by divergence. The divergence of a perfect Gaussian laser beam is defined by the following equation:

$$w(z) = w_0 \sqrt{1 + M^2 \left(\frac{z^2}{z_R^2}\right)}$$

Wherein:
$w(z)$ is the beam radius at a distance z from the beam waist (focal point),
$w_0$ is the radius of the beam waist, and
$z_R$ is the Rayleigh range,
while $M^2$ is the beam propagation factor which is a measure of beam quality.

The Rayleigh range ($z_R$) of a laser beam is defined as the distance over which the beam surface area is doubled and is described by the following equation:

$$z_R = \frac{\pi \cdot w_0^2}{\lambda}$$

Wherein $\lambda$ is the wavelength of the laser beam.

The Rayleigh range is the portion of the beam with the highest intensity, making it the most effective part of the beam for cutting hair because the energy of the laser beam is focussed on a smaller area of the hair. The Rayleigh range, or high intensity region, is represented by the dotted line 18 in FIG. 1 which is in a fixed position. Regions 16, 17 of the beam outside of the Rayleigh range 18 have a larger beam width with a less concentrated energy distribution. Therefore, the hair cutting characteristics of these regions will not be as effective at cutting hair as in the Rayleigh range 18. A well designed laser shaver should not generate a laser beam that is significantly more powerful than required to sever hairs because of power requirements, excessive heat and skin irritation. Therefore, it is important to utilise the high intensity region 18 effectively in a laser shaver.

It will be understood that it is necessary for the laser to operate within predetermined parameters in order to successfully cut hairs by laser absorption. With laser absorption a portion of a hair is exposed to a laser beam in the cutting zone. The portion of the hair exposed to the laser beam is vapourised and/or severed.

Between the first and second reflective elements 5, 10 the cutting section 9 of the laser beam 4 will conform to Gaussian theory and will comprise a 'focal point' 15, or focus spot, located along an optical axis 16 of the beam 4. The focal point 15 is the position of maximum intensity and minimum width and the most effective part of the beam 4 for severing hair because the laser beam energy is concentrated on a smaller area of the hair to be severed, increasing the rate of optical absorption.

In thermal laser shaving driven by optical absorption, the hair is cut by evaporating a slice of the hair. It will be understood that a number of parasitic physical and chemical phenomena occur that impede the hair cutting process. It has been found by experimentation that these parasitic physical and chemical phenomena may be minimised by selecting predetermined parameters. Such parameters ensure that hair received in the cutting zone is cut with a maximum efficiency.

As described above, the cutting section 9 of the laser beam 4 comprises a focal point 15 along the optical axis 16 of the beam 4. The focus spot 15 is the position of maximum intensity and minimum width. Since the laser beam 4 is focused into the focal point 15, the power density of the laser beam will have a maximum value in the focus spot 15. It will be understood that the focus spot 15 will have a horizontal dimension and a vertical dimension. The focus spot dimensions are measured by the distance between points where the intensity falls to $1/e^2 = 0.135$ times the maximum value.

The horizontal spot size dimension is the width of the beam. That is the width of the beam in cross-section defining an axis which extends substantially transverse to the orientation of a hair extending into the cutting zone 8. The vertical spot size dimension is the height of the beam. That is the height of the beam in cross-section defining an axis which extends substantially parallel to the orientation of a hair extending into the cutting zone 8.

In the present embodiments, the width of the beam is determined by the slow optical axis, that is the axis of the beam with the smaller divergence angle; whereas the height of the beam is determined by the fast optical axis; that is the axis of the beam with the larger divergence angle. Therefore, the fast optical axis extends perpendicular to the plane of a user's skin. However, in an alternative embodiment the width of the beam is determined by the fast optical axis, and the height of the beam is determined by the slow optical axis. In such an embodiment the slow optical axis extends perpendicular to the plane of a user's skin.

Experiments have shown that, in order to achieve the mechanical effects resulting from optical absorption with the maximum efficiency, a horizontal spot size value corresponding to the diameter of a hair to be cut is effective. It has been found that the range of the most effective horizontal focus spot size ($1/e^2$) is between 0.05 mm and 1 mm. However, preferably the horizontal focus spot size ($1/e^2$) is between 0.1 mm and 0.5 mm. Furthermore, more preferably the horizontal focus spot size ($1/e^2$) is between 0.15 mm and 0.3 mm. It has been found that a horizontal focus spot size in the above range maximises the rate at which a hair is cut. By providing a horizontal focus spot size with the maximum values provided above, it has been found that this enables the entire width of the beam to impact the hair, without the beam extending beyond the outer edge of the hair and photons not being absorbed by the hair. Furthermore, by providing a horizontal spot size with the above minimum values, it is found that the beam is able to extend across the width of the hair such that the entire width of the hair is exposed to the laser beam. With these threshold values the rate at which the hair is cut by optical absorption is maximised.

Experiments have also shown that, in order to achieve the mechanical effects resulting from optical absorption with the maximum efficiency, a vertical spot size value ($1/e^2$) of less than or equal to 0.2 mm is effective. However, preferably the vertical focus spot size ($1/e^2$) is less than or equal to 0.1 mm. Furthermore, more preferably the vertical focus spot size ($1/e^2$) is less than or equal to 0.05 mm. With a vertical focus spot size below the given threshold it has been found that the effective rate of cutting a hair is maximised. Experimentation has shown that the threshold values provided prevent an unnecessarily larger fraction of the hair from being evaporated through the provision of a laser beam having a too large vertical focus spot size, which may lead to a reduction in cutting efficiency.

It has been found from experimentation that an illumination time, also known as an exposure time, of between 5 ms and 10 ms suffices in order to achieve the mechanical effects of cutting a hair through optical absorption in the focal spot 15.

A characteristic length for the thermal diffusion process follows from an estimation of the range over which the temperature is significantly changed due to thermal transport and is given by:

$L=\sqrt{4\kappa\tau}$

Wherein:
L=characteristic length,
$\kappa$=thermal diffusivity (m²/s),
$\tau$=illumination time.

When the illumination time for a single hair is 10 ms, the characteristic length is between 0.046 mm and 0.06 mm, based on the typical thermal diffusivity of a human hair. Through experimentation it has been found that by providing a vertical spot size in the range of the characteristic length the effective spot size is given by the vertical spot size value of the laser beam and not by the thermal diffusion process.

Experiments have shown that providing a numerical aperture of the laser beam 4 in the cutting zone 8 at or below a predetermined threshold value acts to cut the hair with a maximum efficiency. The numerical aperture of a Gaussian laser beam is related to its spot size at its focal point by:

$$NA \approx \frac{\lambda_0}{\pi w_0}$$

Wherein:
$\lambda_0$ is the vacuum wavelength of the light,
$w_0$ is the diameter of the beam at the focal point.

It has been found that providing a numerical aperture equal to or less than 0.8 is most effective. However, preferably the numerical aperture is equal to or less than 0.6, and more preferably equal to or less than 0.4. By providing a numerical aperture with the given characteristics it is possible to limit having parts of the hair out of the laser focus while the centre of the hair is in focus, as would be caused by selection of a too large numerical aperture.

The size of the focal point 15, together with the numerical aperture, is selected as described above to maximise the effectiveness of the beam 4 for severing hair by concentrating the laser beam energy on a smaller area of the hair to be severed, increasing the rate of optical absorption.

Through experimentation, it has been shown that providing a power density at the focal point above a predetermined threshold enables a hair to be cut through optical absorption with a maximum efficiency. By providing a power density above a threshold value it is possible to minimise the production of phenomena that impedes the hair cutting process. It will be understood that the power density at the focus spot 15 is determined by the combination of the output of the laser generator 2 and the arrangement of the optical system 3.

It has been found that providing a power density at the focus spot 15 is above or equal to 1000 W/cm² is effective. However, preferably a power density at the focus spot 15 is above or equal to 5000 W/cm², and more preferably a power density at the focus spot 15 is above or equal to 50000 W/cm², in order to minimise the production of phenomena that impedes the hair cutting process. For example, melting of the hair, which is not desired since it does not always lead to hair cutting but does consume laser energy, is minimised by providing a power density above the above threshold values.

Experiments have shown that configuring the laser generator 2 in a pulsed operation mode acts to maximise the operating efficiency of the cutting head. It has been found that by configuring the laser generator 2 to operate with pulse duration of greater than or equal to 0.1 microseconds (μs), preferably greater than or equal to 1 μs, and more preferably greater than or equal to 100 μs then a hair is able to be cut by optical absorption, whilst minimising parasitic plasma formation.

It has been found that a suitable upper limit for the pulse duration of the laser generator 2 is 100 milliseconds (ms). However, it will be understood that the laser generator 2 may be operated to have a pulse duration above this limit.

It has also been found that by providing a combination of the above parameters, a synergistic effect occurs to maximise the efficiency of cutting a hair received in the cutting zone 8. Experiments have shown that by providing a combination of some or all of the above parameters it is possible to prevent plasma formation from occurring at a too high fluence. This prevents the plasma from forming an absorbing centre and reducing the fraction of the emitted light that can contribute to the hair cutting process. Therefore, the efficiency of the hair cutting process is maximised. This enables the power requirements of the device to be minimised. This is particularly important in handheld shavers for which a portable power supply is used.

One example of parameters for the laser generator 2 and optical system are given below. In one arrangement, the laser generator 2 is a 3 Watt, 445 nm laser diode. The laser diode is operated in pulse mode with a pulse length of 10 ms. The elliptical laser beam 4 emitted is focused by the optical system 3. The optical system 3 comprises a 30 mm planar convex lens. With such an arrangement, the laser beam is focused from a 4 mm diameter aperture into an efficient cutting focus. The horizontal focus spot size value is about 0.2 mm and the vertical focus spot size value is about 0.02 mm. The numerical aperture value is less than 0.1 with this arrangement. The width of the cutting zone 8 is 12.5 mm in this arrangement, with the laser beam being effective over the full range. In this arrangement the above parameters provide a power density at the focus spot of around 1063 $W/cm^2$.

It is noted that, with the above description, a range of threshold values are provided to achieve successful cutting in the cutting zone by optical absorption whilst ensuring the power output of the laser generator is minimised, i.e. by minimising the parasitic physical and chemical phenomena that can occur to impede cutting of the hair by optical absorption. However, it will be understood that for a given threshold value it is possible to determine other values of the laser generator 2 and optical system 3 in order to achieve the desired effect of cutting by optical absorption.

Figure 2:
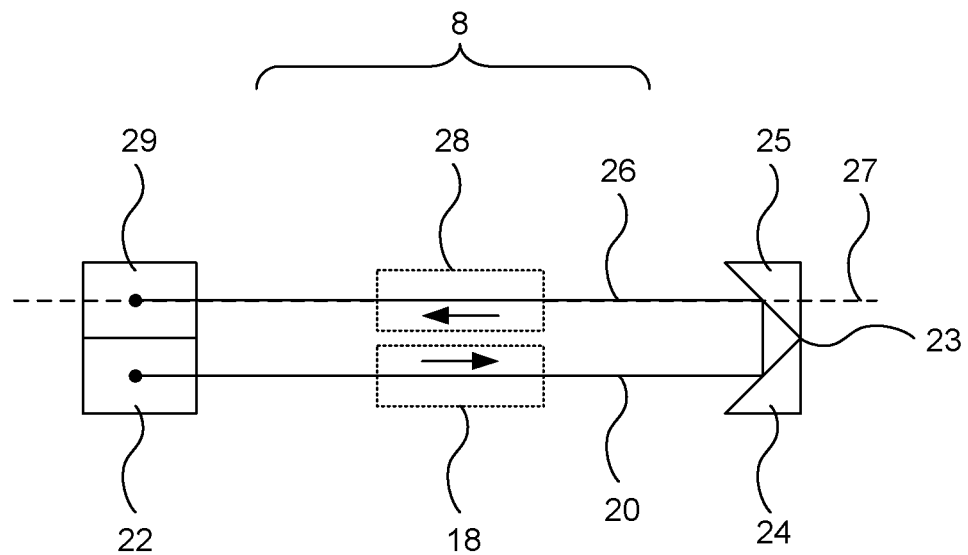
FIG. 2 shows a schematic diagram of part of a head unit for a device for cutting hair in plan view, according to another embodiment.

Although one arrangement of a head unit 1 for a device for cutting hair is described above with reference to FIG. 1, it will be understood that alternative arrangements are envisaged. For example, FIG. 2 shows a top view schematic diagram of another embodiment. This embodiment is generally the same as the embodiment described above and so a detailed description will be omitted herein. The lines representing the laser beam 4 are only representative of the direction of the laser beams and do not show the Gaussian intensity distributions, which would be present. FIG. 2 shows a first reflective element 22 which reflects the first cutting section 20 of the laser beam across the cutting zone 8. The high intensity region 18 is shown in the centre of the cutting zone 8. In this embodiment, the first reflective element 22 is disposed on one side of the cutting zone 8 and a second reflective element 23 is disposed on the opposing side. The second reflective element 23 comprises two portions 24, 25 configured to reflect the cutting section of the laser beam 20 back across the cutting zone 8, to create a second cutting section 26 of the beam that passes through the cutting zone 8, therefore improving the cutting performance of the shaver. The second cutting section 26 of the beam 4 may be reflected along a second optical axis 27 in the cutting zone 8 such that there are two parallel adjacent sections of the laser beam extending across the cutting zone 8. Alternatively, the second cutting section of the beam may be at an angle to the first cutting section of the beam. A third reflective element 29 is disposed to reflect the beam 4 away from the cutting zone 8.

The second reflective element 23 may be configured to focus the second cutting section of the beam 20 within the cutting zone 8 as shown in FIG. 2. For example, when the high intensity region 18 of the first cutting section of the beam 20 is at the centre of the cutting zone 8, the second reflective element 23 is configured such that a high intensity region 28 of the second cutting section 26 of the beam 20 is also at the centre of the cutting zone 8. To focus the second cutting section 26 of the beam 20, an additional focus lens (not shown) may be positioned adjacent to the second reflective element 23.

Optionally, additional subsequent reflective elements (not shown) may be used to reflect the laser beam back across the cutting zone 8 multiple times, allowing the beam to pass for a third, fourth and fifth times across the cutting zone. This will improve the cutting performance of the shaver still further.

With each of the above arrangements, it will be understood that it is possible to apply parameters, i.e. those described above with reference to FIG. 1, to ensure that a hair received in the cutting zone 8 is cut by optical absorption whilst ensuring that the power output of the laser generator is minimised.

The embodiments of shaving device described above relates to shaving the skin to achieve a minimum remaining hair length as well as improved uniformity of remaining hair length. However, the device for cutting hair may alternatively be used for trimming hair to a controlled length that is not necessarily as short as possible, as is the case with a hair trimming or grooming device. To achieve this, the guard would be positioned further from the cutting laser beam(s) so that the cutting height is increased, but remains uniform.

It will be appreciated that the cutting head as described in the above embodiments may be a separate cutting head unit that is attachable to a shaver handle. Therefore, the components described above, for example the laser beam generator, may be located either in the detachable cutting head or in the handle of the shaver. Alternatively, the cutting head may be integrated with a shaver handle as one product.

The cutting head described in the above embodiments may be a separate cutting head unit that is attachable to a shaver handle. The cutting head unit may be removed to clean the cutting head or to replace the cutting head or components of the cutting head after they have become worn.

Although in the above described embodiments the laser generator is configured to operate in a pulsed operation mode, it will be understood that in an alternative embodiment the laser generator is configured to operate in a continuous wave CW mode. By operating the laser generator in a continuous wave mode a simple means of operating the device for cutting hair is provided.

It will be appreciated that the term "comprising" does not exclude other elements or steps and that the indefinite article "a" or "an" does not exclude a plurality. A single processor may fulfil the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalisation thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

The invention claimed is:

1. A cutting head for a device for cutting hair, comprising:
   a laser generator; and
   an optical system configured to focus a laser beam generated by the laser generator and to direct the laser beam along an optical axis across a cutting zone in the cutting head,
   wherein the laser generator and optical system are configured such that, in a focus spot of the laser beam in the cutting zone, a dimension of the focus spot, a power density of the laser beam and a numerical aperture of the laser beam are such that, when a hair is received in the cutting zone, a power output of the laser generator is at a minimum for ensuring that, for a predetermined exposure time, the hair received in the focus spot of the cutting zone is cut by optical absorption, wherein the dimension of the focus spot comprises a horizontal dimension that corresponds with a horizontal focus spot size, and a vertical dimension that corresponds with a vertical focus spot size, wherein the horizontal focus spot size corresponds to a diameter of the hair to be cut, and wherein the numerical aperture is equal to or less than 0.8.

2. The cutting head according to claim 1, further wherein the optical system is further configured such that the numerical aperture is one selected from the group consisting of (i) equal to or less than 0.6, and (ii) equal to or less than 0.4.

3. The cutting head according to claim 1, wherein the optical system is configured such that the vertical focus spot size of the focus spot is one selected from the group consisting of (i) equal to or less than 0.2 mm, (ii) equal to or less than 0.1 mm, and (iii) equal to or less than 0.05 mm.

4. The cutting head according to claim 1, wherein the optical system is configured such that the horizontal focus spot size of the focus spot is one selected from the group consisting of (i) between 0.05 mm and 1 mm, (ii) between 0.1 mm and 0.5 mm, and (iii) between 0.15 mm and 0.3 mm.

5. The cutting head according to claim 1, wherein the power density of the laser beam in the focus spot is one selected from the group consisting of (i) equal to or greater than 1000 $W/cm^2$, (ii) equal to or greater than 5000 $W/cm^2$, and (iii) equal to or greater than 50000 $W/cm^2$.

6. The cutting head according to claim 1, wherein the laser generator is configured to produce a continuous output beam.

7. The cutting head according to claim 1, wherein the laser generator is configured to produce a pulsed output beam.

8. The cutting head according to claim 7, wherein the laser generator is configured to produce the laser beam with a pulse duration selected from the group consisting of (i) greater than or equal to 0.1 μs, (ii) greater than or equal to 1 μs, and (iii) greater than or equal to 100 μs.

9. The cutting head according to claim 1, wherein the optical system is configured such that, during use, a position of the optical axis of the laser beam defined in the cutting head is maintained.

10. The cutting head according to claim 1, further comprising:

a cutting surface against which, during use, a user's skin is locatable, and the optical axis extends substantially parallel to the cutting surface.

11. The cutting head according to claim 1, wherein the optical system further comprises a first reflective element to direct the laser beam across the cutting zone.

12. The cutting head according to claim 1, wherein the optical system further comprises a second reflective element disposed on an opposite side of the cutting zone to the first reflective element to direct the laser beam away from the cutting zone.

13. The cutting head according to claim 1, wherein the optical system comprises a second reflective element disposed on an opposite side of the cutting zone to a first reflective element, the second reflective element being configured to reflect the laser beam back across the cutting zone.

14. A device for cutting hair comprising the cutting head according to claim 1.

15. A method of controlling a cutting head for a device for cutting hair that includes a laser generator and an optical system configured to focus a laser beam generated by the laser generator and to direct the laser beam along an optical axis across a cutting zone in the cutting head, the method comprising:

setting, in a focus spot of the laser beam in the cutting zone, (i) dimension of the focus spot, wherein the dimension of the focus spot comprises a horizontal dimension that corresponds with a horizontal focus spot size, and a vertical dimension that corresponds with a vertical focus spot size, the horizontal focus spot size further corresponding to diameter of the hair to be cut, (ii) a power density of the laser beam and (iii) a numerical aperture of the laser beam such that, when a hair is received in the cutting zone, a power output of the laser generator is at a minimum for ensuring that, for a predetermined exposure time, the hair received in the focus spot of the cutting zone is cut by optical absorption, wherein the numerical aperture is equal to or less than 0.8.

* * * * *